(12) United States Patent
Moriura et al.

(10) Patent No.: US 11,933,797 B2
(45) Date of Patent: Mar. 19, 2024

(54) CALIBRATION CURVE CREATION METHOD, ANALYZER AND NON-TRANSITORY STORAGE MEDIUM

(71) Applicant: SYSMEX CORPORATION, Kobe (JP)

(72) Inventors: Kazuma Moriura, Kobe (JP); Hiroshi Kurono, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 780 days.

(21) Appl. No.: 16/574,740

(22) Filed: Sep. 18, 2019

(65) Prior Publication Data
US 2020/0103428 A1   Apr. 2, 2020

(30) Foreign Application Priority Data
Sep. 28, 2018  (JP) .................................. 2018-185524

(51) Int. Cl.
*G01N 35/00* (2006.01)

(52) U.S. Cl.
CPC .................. *G01N 35/00693* (2013.01); *G01N 2035/00702* (2013.01); *G01N 2035/00891* (2013.01)

(58) Field of Classification Search
CPC ... G01N 35/00693; G01N 2035/00702; G01N 2035/00891; G01N 2201/12746;
(Continued)

(56) References Cited

U.S. PATENT DOCUMENTS 3,960,497 A   6/1976   Acord
4,678,755 A   7/1987   Shinohara et al.
(Continued)

FOREIGN PATENT DOCUMENTS

CN   103217536 A   7/2013
EP   3273250 A1   1/2018
(Continued)

OTHER PUBLICATIONS

Fritsma, Factor Assay Analytical Sensitivity, Apr. 13, 2016, The Fritsma Factor, entire document (Year: 2016).*
(Continued)

*Primary Examiner* — Jill A Warden
*Assistant Examiner* — John McGuirk
(74) *Attorney, Agent, or Firm* — Crowell & Moring LLP

(57) ABSTRACT

Disclosed is a calibration curve creation method performed by an analyzer, the calibration curve creation method including: preparing a plurality of calibrators at different dilution rates by dispensing a calibrator in a container into one or more different containers; obtaining a plurality of measurement values by measuring each of the prepared plurality of calibrators; creating a calibration curve by use of the plurality of measurement values; selecting a first measurement value to be re-measured, among the plurality of measurement values used for the calibration curve; preparing another calibrator at a dilution rate corresponding to a calibrator from which the selected first measurement value is obtained; obtaining a second measurement value by measuring the prepared another calibrator; and creating a new calibration curve by replacing the first measurement value, among the plurality of measurement values, with the second measurement value.

20 Claims, 18 Drawing Sheets

(58) Field of Classification Search
CPC .... G01N 21/82; G01N 33/86; G01N 33/4905; G01N 35/00; G01N 2035/0091
See application file for complete search history.

(56) References Cited

U.S. PATENT DOCUMENTS

| | | | |
|---|---|---|---|
| 2007/0037170 A1* | 2/2007 | Nur | A61P 31/12 435/5 |
| 2011/0301917 A1* | 12/2011 | Kamihara | G01N 35/00693 702/179 |
| 2013/0011298 A1 | 1/2013 | Itou et al. | |
| 2013/0189708 A1 | 7/2013 | Shiba et al. | |
| 2013/0266484 A1 | 10/2013 | Kamihara et al. | |
| 2017/0205435 A1* | 7/2017 | Hagiwara | G01N 35/00603 |
| 2018/0125401 A1 | 5/2018 | Goode, Jr. et al. | |
| 2019/0094249 A1* | 3/2019 | Klingauf | G01N 35/00623 |

FOREIGN PATENT DOCUMENTS

| | | |
|---|---|---|
| JP | S59-116045 A | 7/1984 |
| JP | S61-38464 A | 2/1986 |
| JP | H06-331630 A | 12/1994 |
| JP | 2001-083081 A | 3/2001 |
| JP | 2003-083982 A | 3/2003 |
| JP | 2012-107985 A | 6/2012 |
| JP | 2013-019682 A | 1/2013 |
| JP | 2013-024783 A | 2/2013 |
| JP | 2013-148497 A | 8/2013 |
| JP | 2015-184017 A | 10/2015 |
| WO | WO-2016148166 A1 * | 9/2016 ....... G01N 35/00732 |

OTHER PUBLICATIONS

Hitachi High-Technologies Corporation: "Instruction Manual Hitachi Fluorescence Spectrophotometer FL Solutions Program (Operation Manual)", Nov. 1, 2001, pp. 1-250, Retrieved from the Internet:URL: http://cires1.colorado.edu/jimenez/CHEM-4181/FLSolutionsOperationManual251-9067-2.pdf Retrieved on Feb. 4, 2020.

The extended European search report dated Feb. 13, 2020 in a counterpart European patent application No. 19199503.4.

The Japanese Office Action dated Feb. 12, 2020 in a counterpart Japanese patent application No. 2018-185524.

Communication pursuant to Article 94(3) EPC dated May 20, 2022 in European patent application No. 19199503.4.

Chinese Office Action dated Dec. 9, 2023 in a counterpart Chinese patent application No. 201910935610.3.

* cited by examiner

FIG. 4

| MEASUREMENT ITEM GROUP | REAGENT LOT | CALIBRATOR | CALIBRATOR LOT NUMBER | MEASUREMENT ITEM | DILUTION RATE | MEASUREMENT VALUE |
|---|---|---|---|---|---|---|
| PT-THS | PT THS/OVB 505400/~ | SHP | 502501 | PT THS~% | 1/4 | 28.8 sec |
| | | | | PT THS~% | 1/2 | 17.9 sec |
| | | | | PT THS~% | 1/1 | 12.5 sec |
| | | | | PT INR | 1/4 | ... |
| | | ... | ... | ... | ... | ... |
| AT3 | ... | ... | ... | ... | ... | ... |
| ... | | | | | | |

FIG. 7

CALIBRATION CURVE CREATION

| NEWLY CREATE | ①SELECT MEASUREMENT ITEM GROUP | ②SELECT REAGENT LOT | ③SELECT CALIBRATOR | ④REGISTER ORDER |

A NEW CALIBRATION CURVE IS CREATED.
SELECT A MEASUREMENT ITEM GROUP AND PRESS THE [NEXT] BUTTON. (MULTIPLE MEASUREMENT ITEM GROUPS CAN BE SELECTED).

MEASUREMENT ITEM GROUP

- ☐ VII
- ☐ VIII-FSL
- ☐ INN-DDi
- ☐ vWF-RCo
- ☐ PT
- ☐ Fbg
- ☐ TTO
- ☐ PT-THS

⏮ ◀ ▶ ⏭

ONLY 1 RACK IS NECESSARY.

CANCEL

CALIBRATION CURVE CREATION

| NEWLY CREATE | ①SELECT MEASUREMENT ITEM GROUP | ②SELECT REAGENT LOT | ③SELECT CALIBRATOR | ④REGISTER ORDER |

DESIGNATE A REAGENT LOT OF THE SELECTED MEASUREMENT ITEM GROUP.

MEASUREMENT ITEM GROUP: PT-THS — A30

REAGENT LOT

PT THS /OVB
505400 /-

[NO CALIBRATION CURVE] — A31

⏮ ◀ ▶ ⏭

CANCEL

FIG. 9

CALIBRATION CURVE CREATION

| NEWLY CREATE | ①SELECT MEASUREMENT ITEM GROUP | ②SELECT REAGENT LOT | ③SELECT CALIBRATOR | ④REGISTER ORDER |

ENTER INFORMATION TO BE USED IN CREATION OF THE CALIBRATION CURVE, AND PRESS THE [NEXT] BUTTON.
WHEN THE CALIBRATOR HAS A BAR CODE, READ THE BAR CODE.

| ORDER | MEASUREMENT ITEM GROUP | REAGENT LOT | MEASUREMENT ITEM | CALIBRATOR | LOT NUMBER | EXPIRATION DATE | INDICATION VALUE |
|---|---|---|---|---|---|---|---|
| ☑ | PT-THS | PT THS /OVB 505400 /- | PT THS~% | SHP | 502501 ▶ | --/--/-- | 89.0 % |
| ☑ | PT-THS | PT THS /OVB 505400 /- | PT THS~R | SHP | 502501 ▶ | --/--/-- | % |
| ☑ | PT-THS | PT THS /OVB 505400 /- | PT THS~INR | SHP | 502501 ▶ | --/--/-- | % |

A40 → (points to REAGENT LOT column)
A41 → (points to LOT NUMBER column)

[⏮] [◀] [▶] [⏭]

[NEXT] [CANCEL]

FIG. 16

CALIBRATION CURVE CREATION METHOD, ANALYZER AND NON-TRANSITORY STORAGE MEDIUM

RELATED APPLICATIONS

This application claims priority from prior Japanese Patent Application No. 2018-185524, filed on Sep. 28, 2018, entitled "CALIBRATION CURVE CREATION METHOD AND ANALYZER", the entire content of which is incorporated herein by reference.

BACKGROUND OF THE INVENTION

1. Field of the Invention

The present invention relates to a calibration curve creation method, an analyzer and a non-transitory storage medium.

2. Description of the Related Art

In the field of clinical examination, specimen analyzers that optically measure and analyze the degree of activity and the amount of specific substances contained in specimens such as plasma, serum, and urine are known. In such a specimen analyzer, a calibration curve is created in advance by use of a reference material, called a calibrator, of which concentration and the like are known in advance. Then, a measurement result of a specimen of a subject is compared with the calibration curve created in advance, whereby the specimen of the subject is analyzed.

Japanese Laid-Open Patent Publication No. 2003-083982 discloses an analyzer that can easily determine whether or not a calibration curve is defective, and that can quickly take measures when the calibration curve is defective. The analyzer can be designated in advance to automatically perform retest when the calibration curve is defective. As shown in FIG. 18, when a sample for calibration curve/a sample for validation are set (S1), the analyzer measures the sample for calibration curve and the sample for validation (S2). Subsequently, when the created calibration curve has been determined to be defective (S3: NG) or the calibration curve has been determined to be defective as a result of determination based on the sample for validation (S4: NG), and when the analyzer has been designated in advance to automatically retest the calibration curve (S6: YES), the analyzer automatically returns to the process procedure of step S2 to retest the calibration curve.

For example, in a case of creating a calibration curve for analyzing "PT (prothrombin time) activity %", which is a test item for determining coagulation abnormality of a blood specimen, a plurality of samples created by putting a reagent into each of a plurality of calibrators diluted at different percentages are prepared. Then, a plurality of measurement values obtained by measuring the plurality of samples are plotted on a graph, whereby a calibration curve is created.

Here, for example, when dilution of a part of the plurality of calibrators has failed due to some reason, the calibration curve to be created will include measurement values that will be regarded as errors. Thus, when such a measurement value that is regarded as an error is included in the created calibration curve, accurate measurement cannot be performed with use of the calibration curve. Thus, the calibration curve needs to be corrected.

In the case of the analyzer disclosed in Japanese Laid-Open Patent Publication No. 2003-083982, if the calibration curve has been regarded as an error, all the measurement values need to be measured again. Therefore, when a calibration curve includes a measurement value regarded as an error, the burden of correcting work is increased.

SUMMARY OF THE INVENTION

The scope of the present invention is defined solely by the appended claims, and is not affected to any degree by the statements within this summary.

A calibration curve creation method according to one aspect of the present invention is a calibration curve creation method performed by an analyzer (10). The calibration curve creation method includes: preparing (21) a plurality of calibrators having different dilution rates by dispensing a calibrator in a container into one or more different containers; obtaining (103) a plurality of measurement values by measuring each of the prepared plurality of calibrators; creating (104) a calibration curve by use of the plurality of measurement values; selecting a first measurement value to be re-measured, among the plurality of measurement values used for the calibration curve; preparing (21) another calibrator at a dilution rate corresponding to a calibrator from which the selected first measurement value is obtained; obtaining (103) a second measurement value by measuring the prepared another calibrator; and creating (104) a new calibration curve by replacing the first measurement value, among the plurality of measurement values, with the second measurement value. The calibration curve creation method may further include displaying the plurality of measurement values in association with the dilution ratios, and the selecting the first measurement value may include receiving selection of the first measurement value among the plurality of measurement values displayed in association with the dilution rates.

According to the calibration curve creation method of the present aspect, a new calibration curve can be created by replacing a part of a plurality of measurement values having been used in creation of a calibration curve. Accordingly, a calibration curve that includes a measurement value suspected to be an error can be more quickly corrected. When re-measuring a measurement value, the analyzer prepares a calibrator at a concentration corresponding to the measurement value to be re-measured, and performs measurement by use of the prepared calibrator. Thus, the calibration curve that includes a measurement value suspected to be an error can be more quickly corrected. In addition, the analyzer automatically dilutes a calibrator at a dilution rate corresponding to the measurement value suspected to be an error and performs measurement again. Thus, when compared with a case where a user prepares a calibrator at a dilution rate corresponding to the measurement value suspected to be an error and sets the calibrator to the analyzer, the risk of occurrence of erroneous calibrator preparation can be eliminated, and the calibration curve can be more quickly and accurately corrected.

Each of the measurement values may have a significant figure of not less than 1 digit and not greater than 4 digits. Accordingly, even when a function of automatically diluting a calibrator is used, the accuracy necessary for creation of a calibration curve can be ensured.

The plurality of calibrators having different dilution rates may be each prepared by diluting the calibrator at a dilution rate of less than 100-fold. Accordingly, even when a calibration curve is created by use of the function of automatically diluting a calibrator, the accuracy of the calibration curve can be increased.

Each of the measurement values may be a measurement value of a measurement item for blood coagulation analysis. Accordingly, a calibration curve to be used in blood coagulation analysis can be more quickly and accurately corrected.

The obtaining (103) of the second measurement value may further include: preparing a measurement sample by mixing a reagent for blood coagulation analysis and the prepared another calibrator; and obtaining the second measurement value by measuring the prepared measurement sample. Accordingly, a calibration curve to be used in blood coagulation analysis can be more quickly and accurately corrected.

The calibration curve creation method may further include analyzing (103), by use of the new calibration curve, a measurement value of a specimen collected from a subject. Accordingly, a specimen can be measured by use of the corrected calibration curve, and thus, the specimen can be more accurately measured.

The analysis may be blood coagulation analysis. Accordingly, blood coagulation analysis of a specimen can be more accurately performed by use of the corrected calibration curve.

The calibration curve creation method may further include receiving an instruction from a user through a screen displayed on a display unit. Then, in response to the instruction, the preparing of the calibrator at the dilution rate may be started and the second measurement value may be obtained, and the new calibration curve may be created by replacing the first measurement value with the second measurement value after the second measurement value is obtained. Accordingly, the user can designate to the analyzer the timing at which re-measurement is performed.

An analyzer according to another aspect of the present invention includes: a preparation unit configured to prepare a plurality of calibrators at different dilution rates by dispensing a calibrator in a container into one or more different containers; a measurement unit configured to measure each of the prepared plurality of calibrators to obtain a plurality of measurement values; a controller configured to perform operations including creating a calibration curve by use of the plurality of measurement values; selecting a first measurement value to be re-measured, among the plurality of measurement values used for the calibration curve; causing the preparation unit to prepare another calibrator at a dilution rate corresponding to a calibrator from which the selected first measurement value is obtained; obtaining a second measurement value by measuring the prepared another calibrator by the measurement unit; and creating a new calibration curve by replacing the first measurement value, among the plurality of measurement values, with the second measurement value. The analyzer may further include a display unit, and the controller may perform operations including: causing the display unit to display the plurality of measurement values in association with the dilution ratios; and receiving selection of the first measurement value among the plurality of measurement values displayed in association with the dilution rates.

According to the analyzer of the present aspect, a new calibration curve can be created by replacing a part of a plurality of measurement values having been used in creation of a calibration curve. Accordingly, a calibration curve that includes a measurement value suspected to be an error can be more quickly corrected. When re-measuring a measurement value, the analyzer prepares a calibrator at a concentration corresponding to the measurement value to be re-measured, and performs measurement by use of the prepared calibrator. Thus, the calibration curve that includes a measurement value suspected to be an error can be more quickly corrected. In addition, the analyzer automatically dilutes a calibrator at a dilution rate corresponding to the measurement value suspected to be an error and performs measurement again. Thus, when compared with a case where a user prepares a calibrator at a dilution rate corresponding to the measurement value suspected to be an error and sets the calibrator to the analyzer, the risk of occurrence of erroneous calibrator preparation can be eliminated, and the calibration curve can be more quickly and accurately corrected.

Each of the measurement values may have a significant figure of not less than 1 digit and not greater than 4 digits. Accordingly, even when a function of automatically diluting a calibrator is used, the accuracy necessary for creation of a calibration curve can be ensured.

The plurality of calibrators having different dilution rates may each be prepared by diluting the calibrator at a dilution rate of less than 100-fold. Accordingly, even when a calibration curve is created by use of the function of automatically diluting a calibrator, the accuracy of the calibration curve can be increased.

Each of the measurement values may be a measurement value of a measurement item for blood coagulation analysis. Accordingly, a calibration curve to be used in blood coagulation analysis can be more quickly and accurately corrected.

The preparation unit may prepare a measurement sample by mixing a reagent for blood coagulation analysis and the calibrator. Accordingly, a calibration curve to be used in blood coagulation analysis can be more quickly and accurately corrected.

The analyzer may further analyze, by use of the new calibration curve, a measurement value of a specimen collected from a subject. Accordingly, a specimen of a subject can be analyzed by use of the corrected calibration curve, and thus, the specimen of the subject can be more accurately analyzed.

The analysis may be blood coagulation analysis. Accordingly, blood coagulation analysis of a specimen can be more accurately performed by use of the corrected calibration curve.

The preparation unit may, in responsive to a user instruction, start preparing the calibrator at the dilution rate displayed in association with the selected first measurement value and the measurement unit may obtain the second measurement value, and the creation unit may create the new calibration curve by replacing the first measurement value with the second measurement value after the second measurement value is obtained. Accordingly, the user can designate to the analyzer the timing at which re-measurement is performed.

A non-transitory storage medium according to another aspect of the present invention stores a program executable by a computer to perform operations including: controlling a preparation unit to prepare a plurality of calibrators at different dilution rates by dispensing a calibrator in a container into one or more different containers; controlling a measurement unit to measure each of the prepared plurality of calibrators to obtain a plurality of measurement values; creating a calibration curve by use of the plurality of measurement values; selecting a first measurement value to be re-measured, among the plurality of measurement values used for the calibration curve; controlling the preparation unit to prepare another calibrator at a dilution rate corresponding to a calibrator from which the selected first measurement value is obtained; controlling the measurement unit to measure the prepared another calibrator to obtain a second measurement value; and creating a new calibration curve by replacing the first measurement value, among the plurality of measurement values, with the second measurement value. The program may be executable by the computer to further perform operations of displaying the plurality of measurement values in association with the dilution ratios, and the selecting the first measurement value may include receiving selection of the first measurement value among the plurality of measurement values displayed in association with the dilution rates.

BRIEF DESCRIPTION OF THE DRAWINGS

FIG. 4 shows a specific example of a calibration curve DB;

FIG. 7 shows one example of a screen for receiving selection of a measurement item group for which a calibration curve is to be created;

FIG. 8 shows one example of a screen for designating a lot number of a reagent;

FIG. 9 shows one example of a screen for designating a measurement item and a lot number of a calibrator for which a calibration curve is to be created;

FIG. 16 shows one example of a screen for receiving selection of a measurement item for which a measurement value is to be replaced, and the measurement value;

DETAILED DESCRIPTION OF THE PREFERRED EMBODIMENTS

Figure 1:
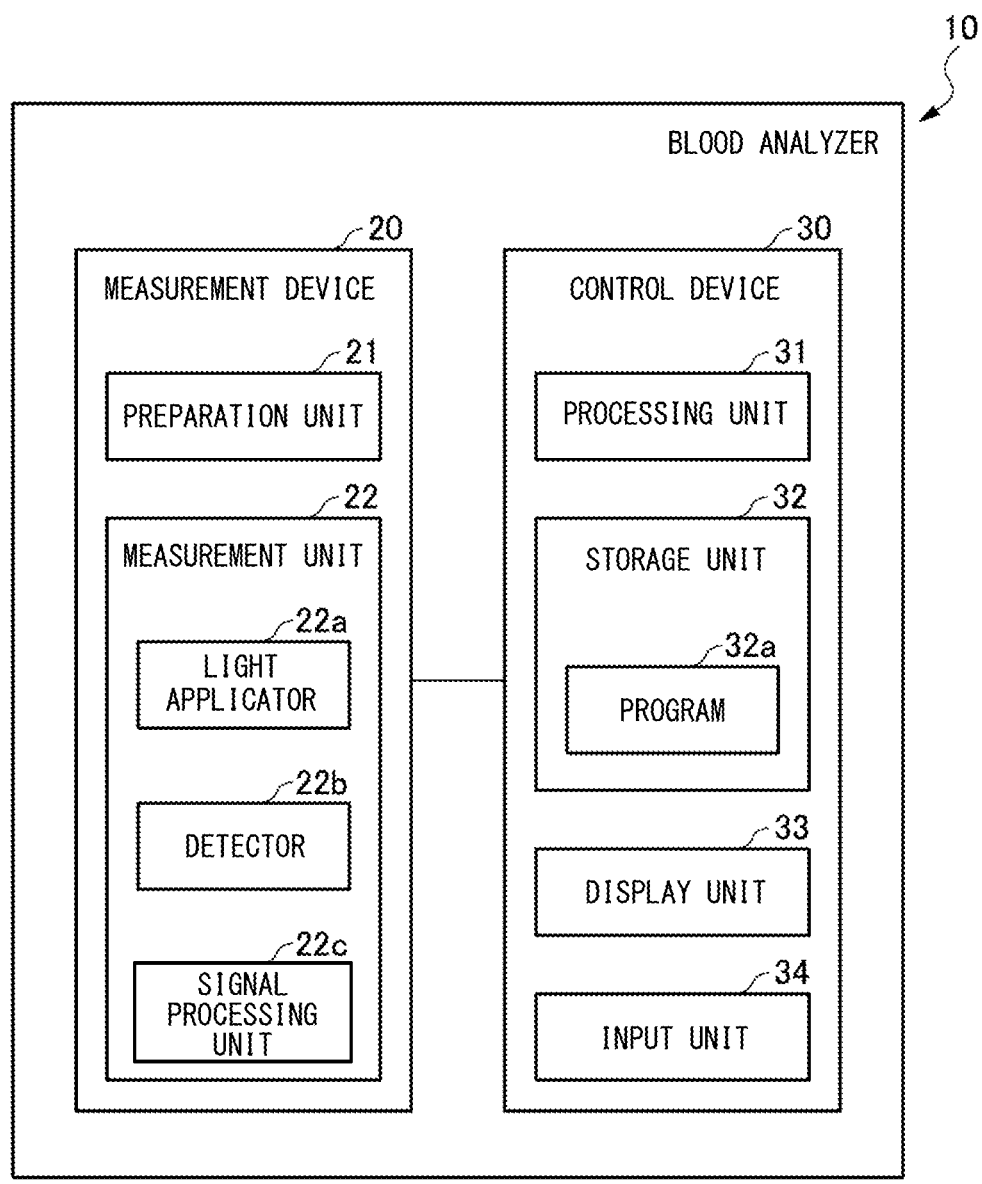
FIG. 1 shows an example of a system configuration of a blood analyzer according to the present embodiment.

A preferable embodiment of the present disclosure will be described with reference to the drawings. In the drawings, components denoted by the same reference character have the same or similar configuration. In the following, described is a process in which a blood analyzer which analyzes blood creates a calibration curve. However, the description does not intend to mean the present embodiment is limited to the blood analyzer. The present embodiment can be applied to any analyzer that creates a calibration curve.

<System Configuration>

FIG. 1 shows an example of a system configuration of a blood analyzer according to the present embodiment. As shown in FIG. 1, a blood analyzer 10 includes a measurement device 20 and a control device 30. The blood analyzer 10 applies light to a blood sample prepared by adding a reagent to a blood specimen, and performs analysis regarding coagulability of the blood specimen by analyzing the obtained transmitted light according to a coagulation method, a synthetic substrate method, immunonephelometryA, and an agglutination method, thereby being able to obtain measurement results for a plurality of measurement items.

The measurement device 20 includes a preparation unit 21 and a measurement unit 22. The preparation unit 21 dispenses a blood specimen from a specimen container, heats the dispensed blood specimen, and adds a reagent to the heated blood specimen, to prepare a blood sample. The measurement unit 22 includes a light applicator 22a, a detector 22b, and a signal processing unit 22c. The light applicator 22a applies light to a blood sample prepared by the preparation unit 21. The light applicator 22a is a halogen lamp or an LED, for example. The detector 22b receives light that has been transmitted through the blood sample, out of the light that has been applied to the blood sample by the light applicator 22a. The detector 22b is a photodiode or an avalanche photodiode, for example.

When coagulation reaction of a blood sample advances, the turbidity of the blood sample increases, and in accordance with the increase of the turbidity, the amount of transmitted light from the blood sample decreases. The detector 22b detects the process of coagulation of blood, as a change of the transmitted light. In this case, when the coagulation reaction of the blood sample advances, the amount of light received by the detector 22b decreases, in general. It should be noted that in a case where the detector 22b receives scattered light, when the coagulation reaction of a blood sample advances, the amount of light received by the detector 22b increases, in general.

The signal processing unit 22c converts a detection signal outputted by the detector 22b into digital data by means of an AD converter, and transmits the resultant digital data to the control device 30. The data transmitted to the control device 30 is data (hereinafter, referred to as "time series data") that changes in accordance with a lapse of time in a detection period from the start to the end of detection performed by the detector 22b. In a case where a coagulation method is used as the measurement method, the time series data is obtained by detecting the process of coagulation of the blood sample as a chronological change of the intensity of transmitted light, and the time series data is coagulation curve data.

Figure 2:
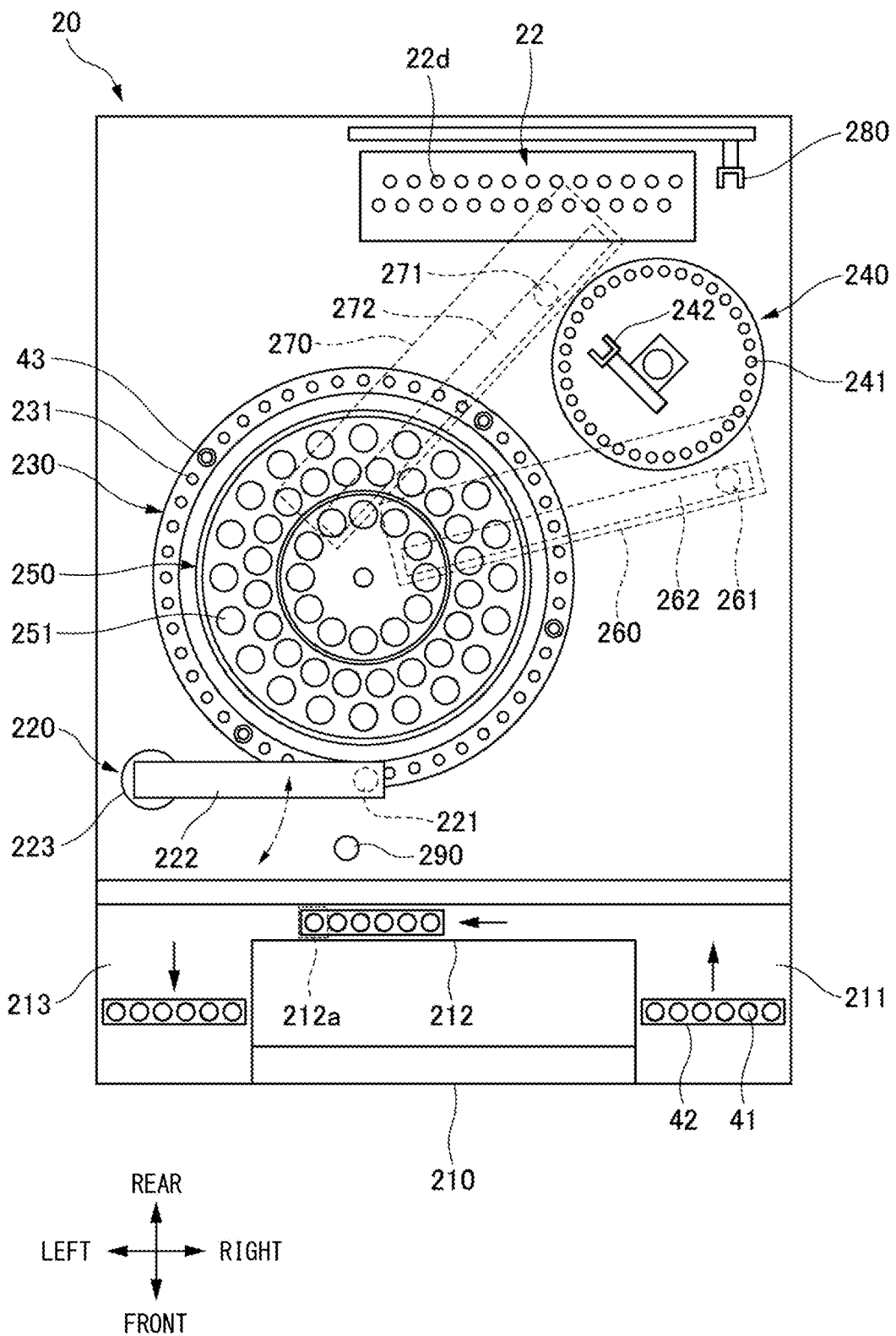
FIG. 2 is a schematic plan view of a configuration of the blood analyzer according to the present embodiment.

FIG. 2 shows a configuration of the measurement device 20 in FIG. 1, viewed from above. The measurement device 20 includes components shown in FIG. 2 in addition to the components shown in FIG. 1.

As shown in FIG. 2, the measurement device 20 includes a transport unit 210, a specimen dispenser 220, a reaction chamber table 230, a heating table 240, a reagent table 250, reagent dispensers 260, 270, a transfer unit 280, and the measurement unit 22.

The transport unit 210 includes a rack setting part 211, a rack transporter 212, and a rack collection part 213. An operator sets specimen containers 41 each containing a blood specimen, to a specimen rack 42, and places the specimen rack 42 on the rack setting part 211. The transport unit 210 transports the specimen rack 42 placed on the rack setting part 211, to the rack transporter 212, and sequentially locates a specimen container 41 at a specimen suction position 212a. Upon completion of the suction of the specimen from all the specimen containers 41 held in the specimen rack 42, the transport unit 210 transports the specimen rack 42 to the rack collection part 213. The number of specimen containers 41 that can be held in one specimen rack 42 is not limited to 6, and may be another number.

The specimen dispenser 220 includes a nozzle 221, an arm 222, and a mechanism unit 223. The nozzle 221 is provided to the leading end of the arm 222. The mechanism unit 223 is configured to rotate the arm in the circumferential direction and to move the arm in the up-down direction. Accordingly, the nozzle 221 can move in the circumferential direction and the up-down direction. The specimen dispenser 220 suctions a blood specimen from a specimen container 41 located at the specimen suction position 212a, and discharges the suctioned specimen into a reaction chamber 43 held in a holding hole 231 of the reaction chamber table 230.

The reaction chamber table 230 has a ring shape in a plan view, and is disposed outside the reagent table 250. The reaction chamber table 230 is configured to be rotatable in the circumferential direction. The reaction chamber table 230 has a plurality of holding holes 231 each for holding a reaction chamber 43.

The heating table 240 includes a plurality of holding holes 241 each for holding a reaction chamber 43, and a transfer unit 242 for transferring a reaction chamber 43. The heating table 240 has a circular contour in a plan view, and is configured to be rotatable in the circumferential direction. The heating table 240 heats reaction chambers 43 set in holding holes 241 to 37° C.

When the blood specimen is discharged into a reaction chamber 43 held on the reaction chamber table 230, the reaction chamber table 230 is rotated, and the reaction chamber 43 containing the blood specimen is transferred to the vicinity of the heating table 240. Then, the transfer unit 242 of the heating table 240 grips this reaction chamber 43, and sets the reaction chamber 43 into a holding hole 241 of the heating table 240.

The reagent table 250 is configured such that a plurality of reagent containers 251 each containing a reagent to be used in measurement for a blood coagulation test can be placed thereon. The reagent table 250 is configured to be rotatable in the circumferential direction. On the reagent table 250, a plurality of reagent containers 251 each containing a reagent to be used in measurement for a measurement item are placed. For example, a reagent container 251 containing a reagent for prothrombin time measurement, a reagent container 251 containing a reagent for fibrinogen measurement, and the like are placed on the reagent table 250.

The reagent dispenser 260 includes a nozzle 261 and a mechanism unit 262. The mechanism unit 262 is configured to move the nozzle 261 in the horizontal direction so as to cross the reagent table 250, and is configured to move the nozzle 261 in the up-down direction. Similarly, the reagent dispenser 270 includes a nozzle 271 and a mechanism unit 272. The mechanism unit 272 is configured to move the nozzle 271 in the horizontal direction so as to cross the reagent table 250, and is configured to move the nozzle 271 in the up-down direction. The reagent dispensers 260 and 270 are provided at the lower side of the upper face of the housing of the measurement device 20.

The reagent dispenser 260, 270 dispenses a reagent into a reaction chamber 43 heated on the heating table 240. When dispensing a reagent, the transfer unit 242 or the transfer unit 280 takes out a reaction chamber 43 from a holding hole 241 of the heating table 240, and locates the reaction chamber 43 to a predetermined position in the vicinity of the heating table 240. Then, the reagent dispenser 260, 270 suctions a reagent through the nozzle 261, 271 from a reagent container 251, and discharges the suctioned reagent into the reaction chamber 43. Accordingly, the reagent is mixed with the blood specimen, whereby a blood sample is prepared. The preparation unit 21 shown in FIG. 1 corresponds to the heating table 240, the reagent table 250, the reagent dispensers 260, 270, and the transfer unit 280. Then, the transfer unit 280 sets the reaction chamber 43 into a holding hole 22d of the measurement unit 22.

The measurement unit 22 includes a plurality of holding holes 22d. The measurement unit 22 applies light by means of the light applicator 22a, to the reaction chamber 43 set in the holding hole 22d, and receives, by means of the detector 22b, light having been transmitted through the blood sample. The detector 22b detects the process of coagulation of blood, as a change of the transmitted light.

When measuring a calibrator in order to create a calibration curve, the measurement device 20 performs operations of automatically diluting a set calibrator to a concentration necessary for creation of a calibration curve and then measuring the coagulation process, in addition to the operations described above. More specifically, the nozzle 221 moves to the specimen suction position 212a, and suctions the calibrator from the specimen container 41 located at the specimen suction position 212a. Subsequently, the nozzle 221 moves to the position of a diluent container 290, and suctions the diluent from the diluent container 290, thereby diluting the calibrator in the nozzle to a predetermined concentration. Subsequently, the nozzle 221 discharges the diluted calibrator into a reaction chamber 43 held in a holding hole 231 of the reaction chamber table 230. The measurement device 20 repeats, a number of times necessary for creation of a calibration curve, a series of operations of: dispensing the calibrator diluted through the above procedure from the same specimen container 41 into the reaction chamber 43; heating the reaction chamber 43; injecting a reagent into the reaction chamber 43; and measuring the coagulation process.

The control device 30 includes a processing unit 31, a storage unit 32, a display unit 33, and an input unit 34. The processing unit 31 is a CPU, for example. The storage unit 32 is a RAM, a ROM, a hard disk, or the like, for example. The storage unit 32 stores therein a computer program 32a to be executed by the processing unit 31.

The processing unit 31 processes the detection result of the measurement unit 22. Specifically, the processing unit 31 obtains, from the measurement device 20, time series data obtained by measuring a blood specimen or a calibrator, and calculates a measurement value (coagulation time or absorbance change amount) which corresponds to a measurement item for blood coagulation analysis, by use of the obtained time series data.

The processing unit 31 creates a calibration curve by plotting a plurality of measurement values obtained by use of calibrators having different concentrations, onto a two-axes graph having one axis (for example, X-axis) representing concentration and the other axis (for example, Y-axis) representing measurement value. In the description below, the point plotted on the graph may be referred to as "calibration curve point". The calibrator is a reference material that is used in order to create a calibration curve. The calibrator is plasma or the like collected from a healthy subject, for example.

A calibration curve is a standard curve that is referred to when a specimen of a subject is measured. In general, it is considered that a calibration curve needs to be created every time the reagent lot is changed. This is because, even when the same reagent and the same specimen are used, if the reagent lot is different, the measurement value could vary.

The display unit 33 is a liquid crystal display, for example. The input unit 34 is a mouse and a keyboard. As in the case of a touch panel-type display, the display unit 33 and the input unit 34 may be integrated to each other.

<Function Block Configuration>

Figure 3:
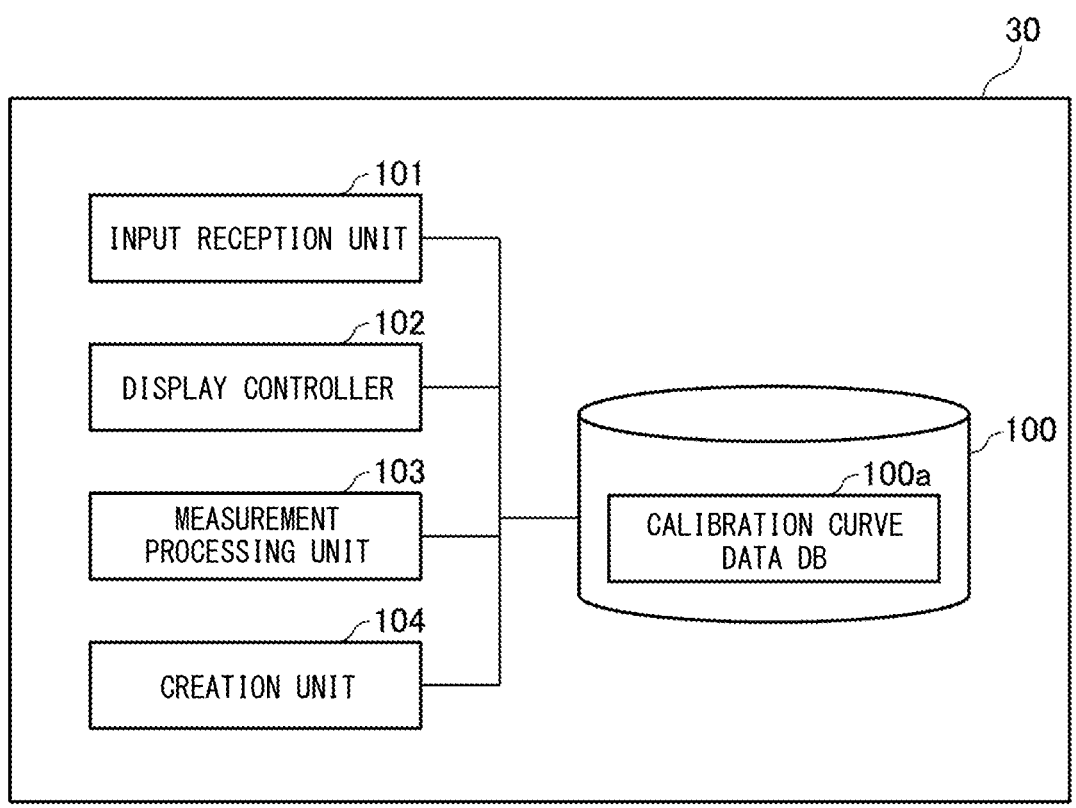
FIG. 3 shows an example of a function block configuration of a control device according to the present embodiment.

FIG. 3 shows an example of a function block configuration of the control device 30 according to the present embodiment. The control device 30 includes a DB (data base) 100, an input reception unit 101, a display controller 102, a measurement processing unit 103, and a creation unit 104. The DB 100 stores a calibration curve DB 100a therein. The input reception unit 101, the display controller 102, the measurement processing unit 103, and the creation unit 104 can be realized by the processing unit 31 of the control device 30 executing the program 32a stored in the storage unit 32. The program 32a can be stored in a storage medium. The storage medium storing the program 32a may be a non-transitory computer readable storage medium. The non-transitory storage medium is not limited in particular, but may be a storage medium such as a USB memory or a CD-ROM, for example.

The input reception unit 101 has a function of receiving various types of data inputted to the control device 30 by a user operating the input unit 34. For example, the input reception unit 101 receives, from the user, an instruction to create a calibration curve, selection of a measurement value (first measurement value) for which measurement is to be performed again among a plurality of measurement values having been used in creation of a calibration curve, an instruction to start re-measurement, and the like.

The display controller 102 has a function of: generating various types of screens to be used in operations performed on the blood analyzer 10; and causing the display unit 33 to display the generated screens. The screens generated by the display controller 102 include, for example, a screen for receiving selection of a measurement value for which measurement is to be performed again among a plurality of measurement values having been used in creation of a calibration curve, a screen for receiving, from the user, an instruction to start re-measurement, and the like.

The measurement processing unit 103 obtains, from the measurement device 20, time series data obtained by measuring each of a plurality of calibrators (samples) having different concentrations, and calculates a measurement value (coagulation time, absorbance change amount, etc.) for each calibrator (sample) by use of the obtained time series data. In a case where the input reception unit 101 has received selection of a measurement value (first measurement value) for which measurement is to be performed again, the measurement processing unit 103 instructs the measurement device 20 to perform measurement again for the calibrator having the concentration corresponding to the selected measurement value, obtains, from the measurement device 20, time series data obtained through the re-measurement, and calculates a measurement value.

The creation unit 104 has a function of creating a calibration curve by use of the measurement value for each of a plurality of calibrators having different concentrations, the measurement value having been calculated by the measurement processing unit 103.

The creation unit 104 has a function of creating a new calibration curve by replacing a part (first measurement value), designated by the user, of a plurality of measurement values having been used in creation of a calibration curve, with a measurement value (second measurement value) obtained by measuring again a calibrator (sample) having the same concentration as that corresponding to the designated measurement value.

The creation unit 104 stores, in the calibration curve DB 100a, measurement values having been used in creation of a calibration curve, and information regarding reagents having been used in creation of the calibration curve and items and the like for which measurement has been performed, for example.

FIG. 4 shows a specific example of the calibration curve DB 100a. In "measurement item group", a collective name of a group of one or a plurality of measurement items is stored. For example, in the example shown in FIG. 4, the measurement item group "PT THS" is a group that includes measurement items such as PT THS-% and PT INR. In "reagent lot", information indicating the lot of a reagent to be used in measurement for a calibration curve is stored. Here, the lot is information that indicates a production unit. Having the same lot means that the production unit specified according to plant, season, or the like of the production is the same, for example. In "calibrator", the name (for example, trade name or the like of commercially available plasma) of a standard plasma or the like to be used in creation of the calibration curve is stored. In "calibrator lot number", a lot number provided for each calibrator is stored. In "measurement item", the name of a measurement item corresponding to the calibration curve is stored. "Dilution rate" indicates a dilution rate at which the calibrator is diluted. For example, 1/1 means that no dilution has been performed, and ½ means that a diluent and the calibrator have been mixed at a ratio of 1 to 1. In "measurement value", a measurement value corresponding to the measurement item and the dilution rate is stored.

<Process Procedure>

(Creation of Calibration Curve)

Figure 5:
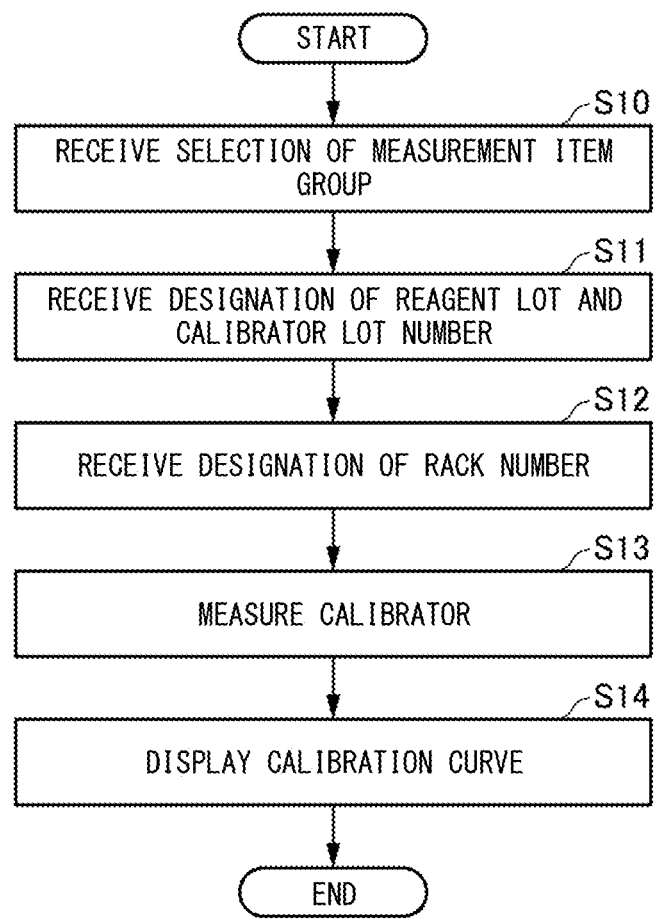
FIG. 5 is a flow chart showing one example of a process procedure in which the blood analyzer creates a calibration curve.

FIG. 5 is a flow chart showing one example of the process procedure in which the blood analyzer 10 creates a calibration curve. In the description below, it is assumed that the blood analyzer 10 automatically creates a calibration curve by measuring a calibrator while automatically diluting the calibrator with a diluent.

Figure 6:
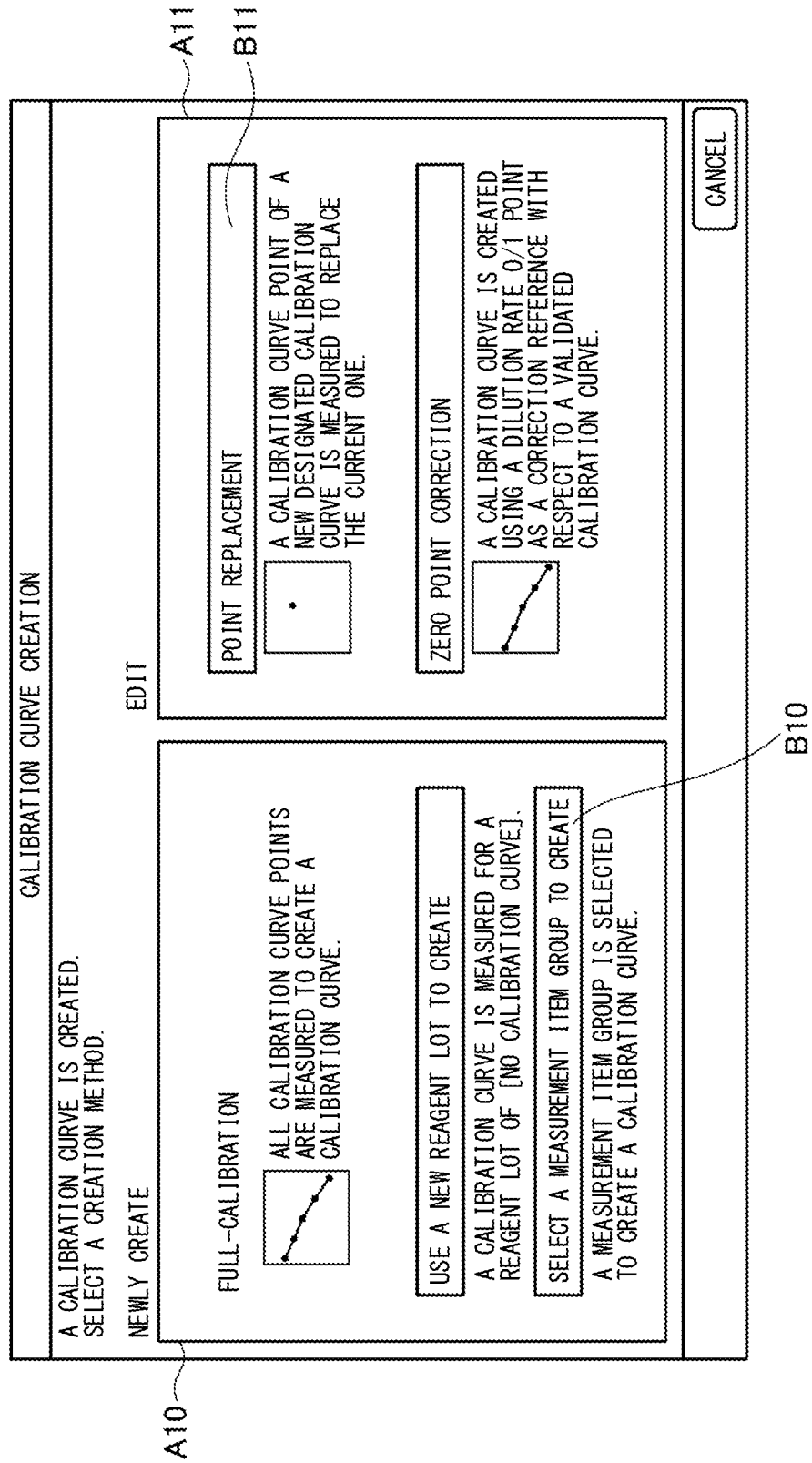
FIG. 6 shows one example of a menu screen of the blood analyzer.

In step S10, the input reception unit 101 receives selection of a measurement item group for which a calibration curve is to be created. FIG. 6 shows one example of a menu screen of the blood analyzer 10, and FIG. 7 shows one example of a screen for receiving selection of a measurement item group for which a calibration curve is to be created. The screen shown in FIG. 6 includes a display area A10 in which a selection button B10 to be used when newly creating a calibration curve is displayed, and a display area A11 in which a selection button B11 to be used when replacing a part of measurement values of the created calibration curve is displayed. When the button B10 is pressed, the screen shifts to the screen shown in FIG. 7. On the screen shown in FIG. 7, a display area A20 for receiving selection of a measurement item group is displayed, and the user can select a desired measurement item group from among a plurality of measurement item groups displayed in the display area A20. With reference back to FIG. 5, description is continued.

In step S11, with respect to the measurement item group selected in the process procedure of step S10, the input reception unit 101 receives designation of the lot of a reagent and a lot number of a calibrator to be used in creation of a calibration curve. FIG. 8 shows an example of a screen for designating a lot number of a reagent. The screen shown in FIG. 8 includes a display area A30 for displaying the measurement item group selected on the screen in FIG. 7, and a display area A31 for displaying a list of reagent lots of reagents registered in advance in the blood analyzer 10, among the reagents to be used in measurement for the selected measurement item group. When one reagent lot has been selected in the display area A31, the screen shifts to the screen show in FIG. 9. The screen shown in FIG. 9 includes a display area A40 for receiving designation of a measurement item for which a calibration curve is to be created, and an input area A41 for receiving designation of a lot number of a calibrator to be used in creation of the calibration curve. With reference back to FIG. 5, description is continued.

Figure 10:
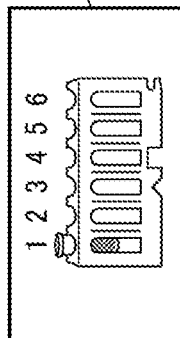
FIG. 10 shows one example of a screen for receiving designation of a specimen rack holding a specimen container.

In step S12, the input reception unit 101 receives, from the user, an input of a rack number of a specimen rack 42 in which a specimen container 41 holding a calibrator is inserted. FIG. 10 shows one example of a screen for receiving an input of a rack number. The screen shown in FIG. 10 includes an input area A50 for inputting a rack number of a specimen rack 42, and a display area A51 for designating to the user a position at which the specimen container 41 should be inserted, among a plurality of insertion positions (six in the example in FIG. 10) of the specimen rack 42 having the inputted rack number.

In step S13, the measurement unit 22 performs measurement of the calibrator, using the calibrator in the specimen container 41 held at the rack position designated in the process procedure of step S12, and the reagent having the lot number designated in the process procedure of step S11. The measurement processing unit 103 calculates a measurement value by use of time series data obtained through measurement by the measurement unit 22.

Figure 11:
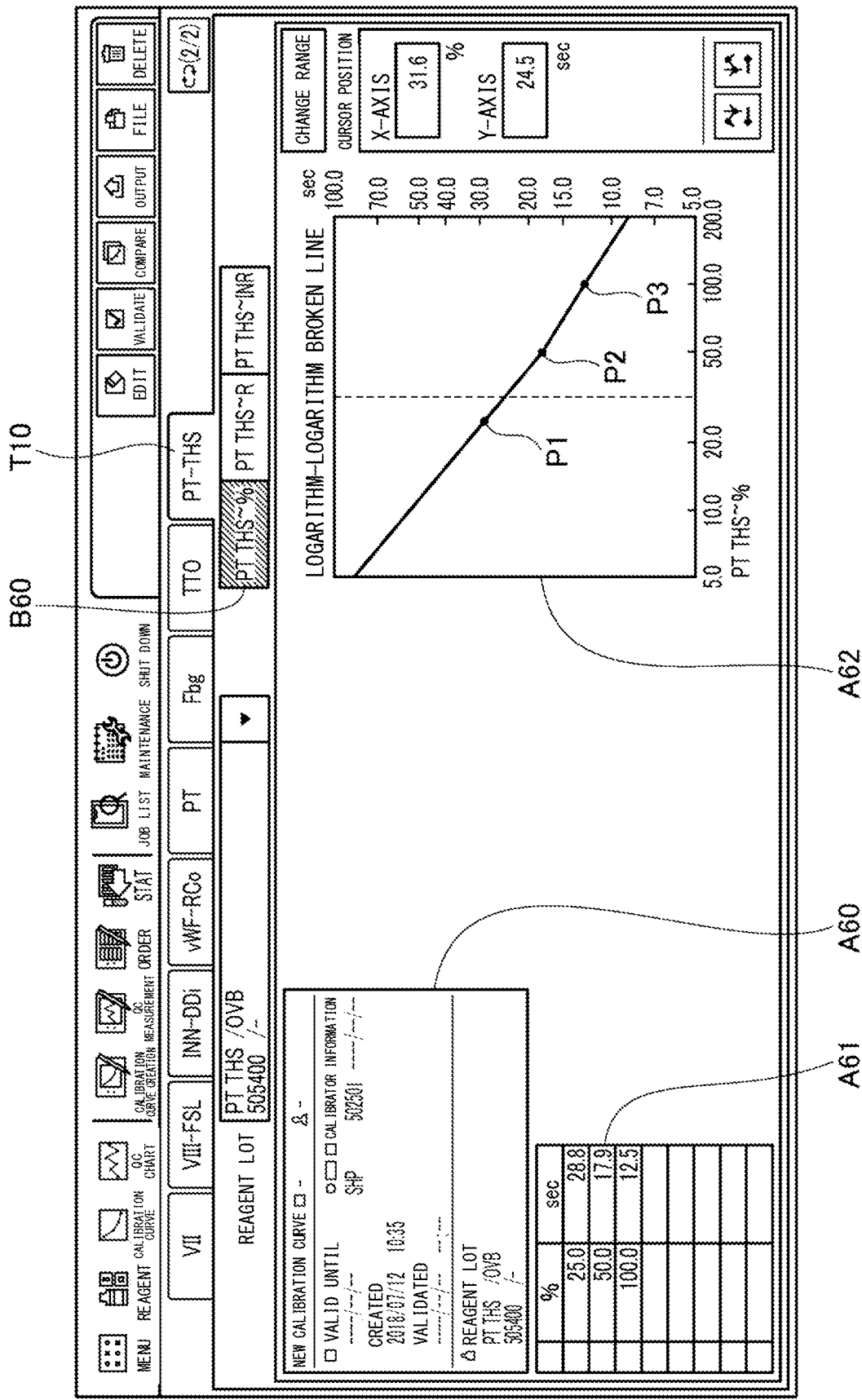
FIG. 11 shows one example of a screen for displaying a calibration curve.

In step S14, the display controller 102 causes the display unit 33 to display a screen for displaying a calibration curve. FIG. 11 shows one example of the screen for displaying a calibration curve. In a display area A60, information (lot number and the like) regarding the calibrator used in creation of the calibration curve is displayed. In a display area A61, a list of a concentration and a measurement value is displayed for each calibration curve point. The calibration curve is displayed in a display area A62. In FIG. 11, three calibration curve points, i.e., P1, P2, and P3, are present. P1 indicates a measurement value when the concentration is 25% (diluted 4-fold). P2 indicates a measurement value when the concentration is 50% (diluted 2-fold). P3 indicates a measurement value when the concentration is 100% (not diluted). A tab T10 receives selection of a measurement item group for which a calibration curve is displayed. A button B60 receives selection of a measurement item for which a calibration curve is displayed, in the measurement item groups selected by means of the tab T10.

(Details of Method for Measuring Calibrator)

Figure 12:
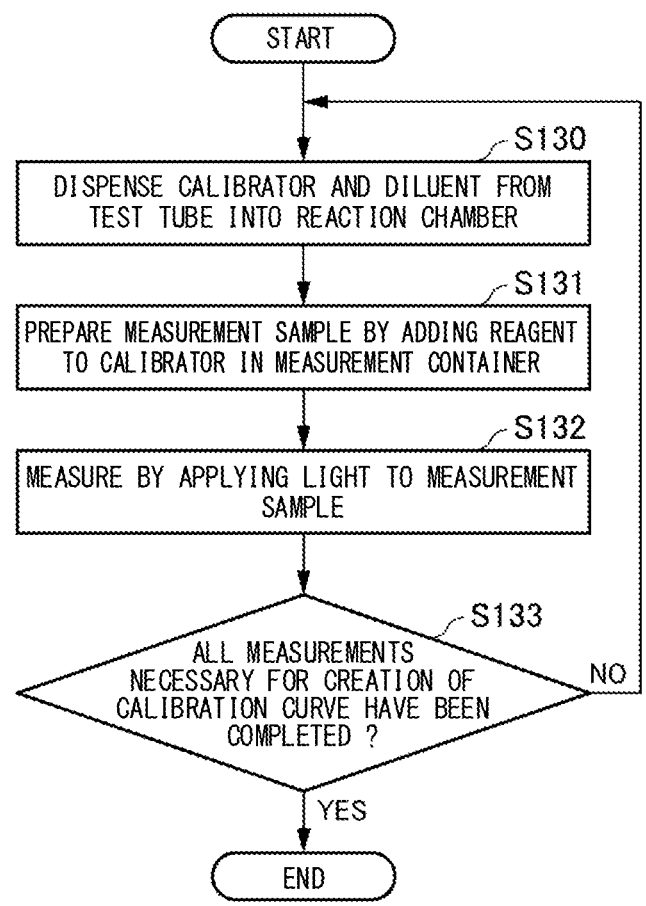
FIG. 12 shows one example of a process procedure in detail in which the blood analyzer measures a calibrator.

FIG. 12 shows in detail one example of a process procedure in which the blood analyzer 10 performs measurement of a calibrator. With reference to FIG. 12, details of the process procedure performed by the measurement unit 22 and the measurement processing unit 103 in the process procedure of step S13 in FIG. 5 are described.

In step S130, the preparation unit 21 suctions some of the calibrator from the specimen container 41 (container, first container) inserted at the position indicated in the process procedure of step S12, dilutes the suctioned calibrator to a predetermined dilution rate by adding a diluent thereto, and then dispenses the diluted calibrator to a reaction chamber (different container, second container). It should be noted that the dilution rate and the concentration can be convertible with each other, and the relationship is 100/dilution rate=concentration (%). For example, a dilution rate of 2-fold is the same as a concentration of 50%. In step S131, the preparation unit 21 prepares a measurement sample by mixing the diluted calibrator in the reaction chamber and a reagent for blood coagulation analysis together. In step S132, by applying light to the generated measurement sample, the measurement unit 22 measures change in the transmitted light and change in the absorbance and transmits time series data obtained through the measurement, to the control device 30. The measurement processing unit 103 having received the time series data analyzes the time series data by use of a predetermined algorithm, thereby calculating a measurement value (coagulation time, absorbance change amount, or the like of the calibrator).

The measurement unit 22 and the measurement processing unit 103 repeat the process procedure of step S130 to step S132, to obtain a plurality of pairs of a concentration and a measurement value of the calibrator (for example, the coagulation time at a concentration of 20% is 28 seconds, etc.), which are necessary for creation of a calibration curve. The levels of the concentration (dilution rate) of the calibrator to be used in creation of a calibration curve may be determined in advance. For example, three levels of a concentration of 25% (dilution rate: 4-fold), a concentration of 50% (dilution rate: 2-fold), and a concentration of 100% (dilution rate: 1-fold) may be used, or further finer levels may be specified. When having completed all measurements necessary for creation of a calibration curve (S133), the measurement unit 22 and the measurement processing unit 103 end the process.

The number of significant figures of the measurement value calculated by the measurement processing unit 103 may be 1 digit or more and not greater than 4 digits, or may be 1 decimal place. The dilution rate at which the measurement unit 22 dilutes the calibrator may be less than 100-fold (1/100, concentration of 1%).

(Replacement of Measurement Value)

The user confirms the calibration curve displayed on the screen shown in FIG. 11, and confirms the presence or absence of an abnormal measurement value. An abnormality of the measurement value could occur, for example, when the amount of the calibrator set in a specimen container 41 was smaller than the prescribed amount and thus the calibrator was not diluted to an accurate concentration, or when poor dissolution or poor mixing was caused due to some reason at the time of addition of a diluent or a reagent to the calibrator. In this case, the blood analyzer 10 replaces the measurement value having been determined to be abnormal by the user, among the plurality of measured measurement values, with a measurement value obtained by measuring the calibrator again, thereby creating a more accurate calibration curve.

Figure 13:
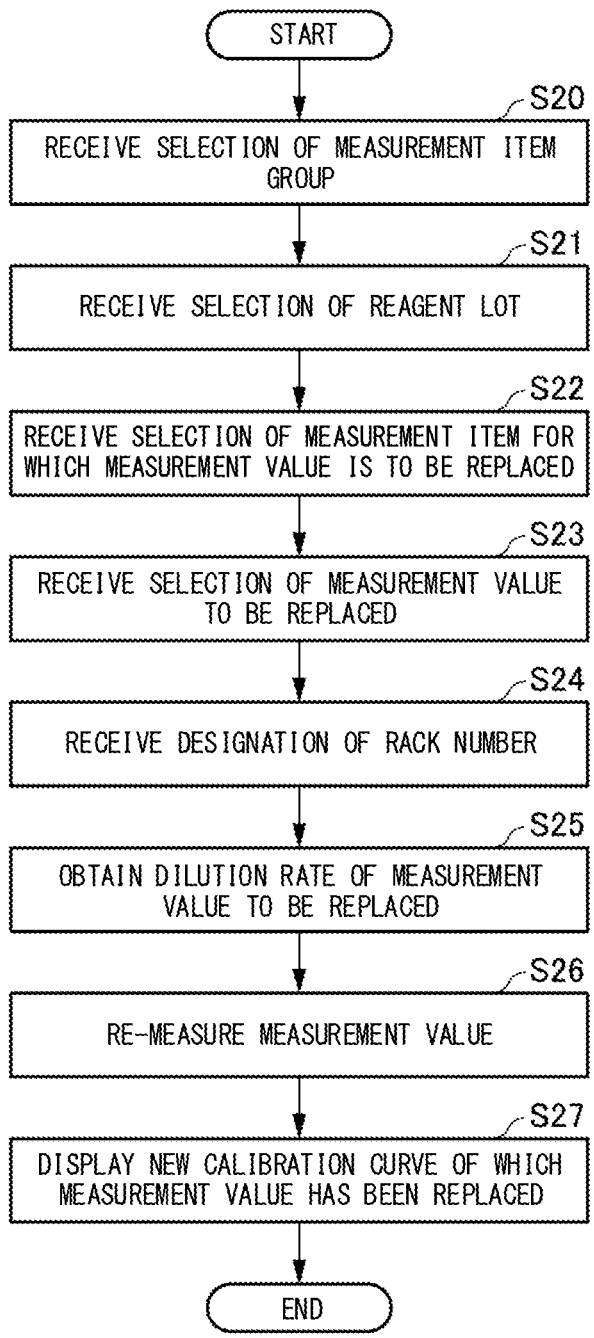
FIG. 13 is a flow chart showing one example a process procedure in which the blood analyzer replaces a measurement value of a calibration curve.

FIG. 13 is a flow chart showing one example of a process procedure in which the blood analyzer 10 replaces a measurement value of a calibration curve. The process procedure shown in the flow chart is started when the selection button B11 is pressed on the screen shown in FIG. 6.

In step S20, the input reception unit 101 receives selection of a measurement item group for a calibration curve of which a measurement value is to be replaced, among created calibration curves. Next, in step S21, the input reception unit 101 receives selection of a reagent lot having been used in creation of the calibration curve of which a measurement value is to be replaced.

Figure 14:
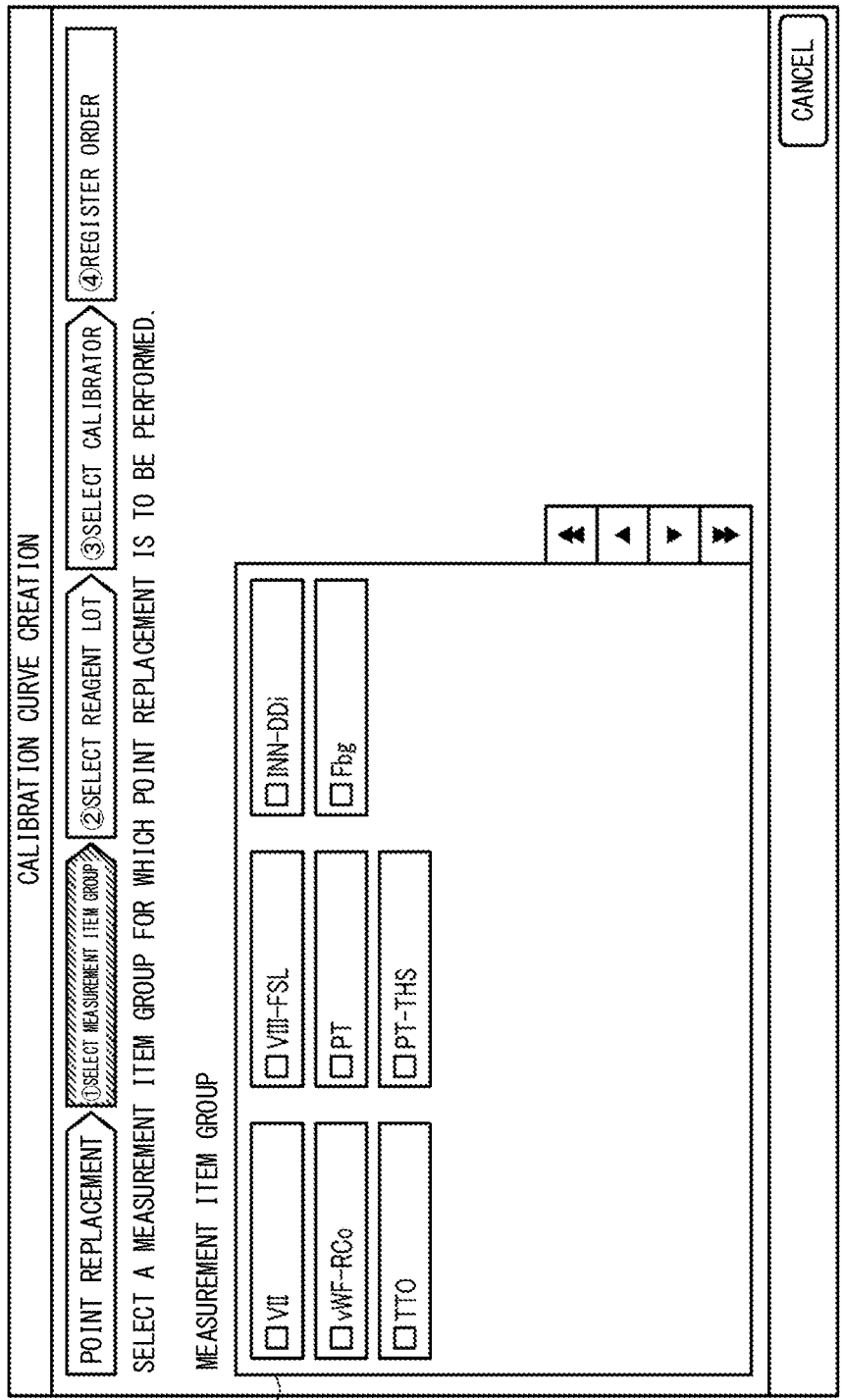
FIG. 14 shows one example of a screen for receiving selection of a measurement item group.

Here, one example of a screen for receiving selection of a measurement item group is shown in FIG. 14. The screen shown in FIG. 14 includes a display area A70 for displaying a list of measurement item groups for which calibration curves have already been created. As described above, the calibration curve DB 100a stores data regarding created calibration curves. The display controller 102 refers to the calibration curve DB 100a, extracts measurement item groups recorded in "measurement item group" of the calibration curve DB 100a, and displays a list of the extracted measurement item groups in the display area A70.

Figure 15:
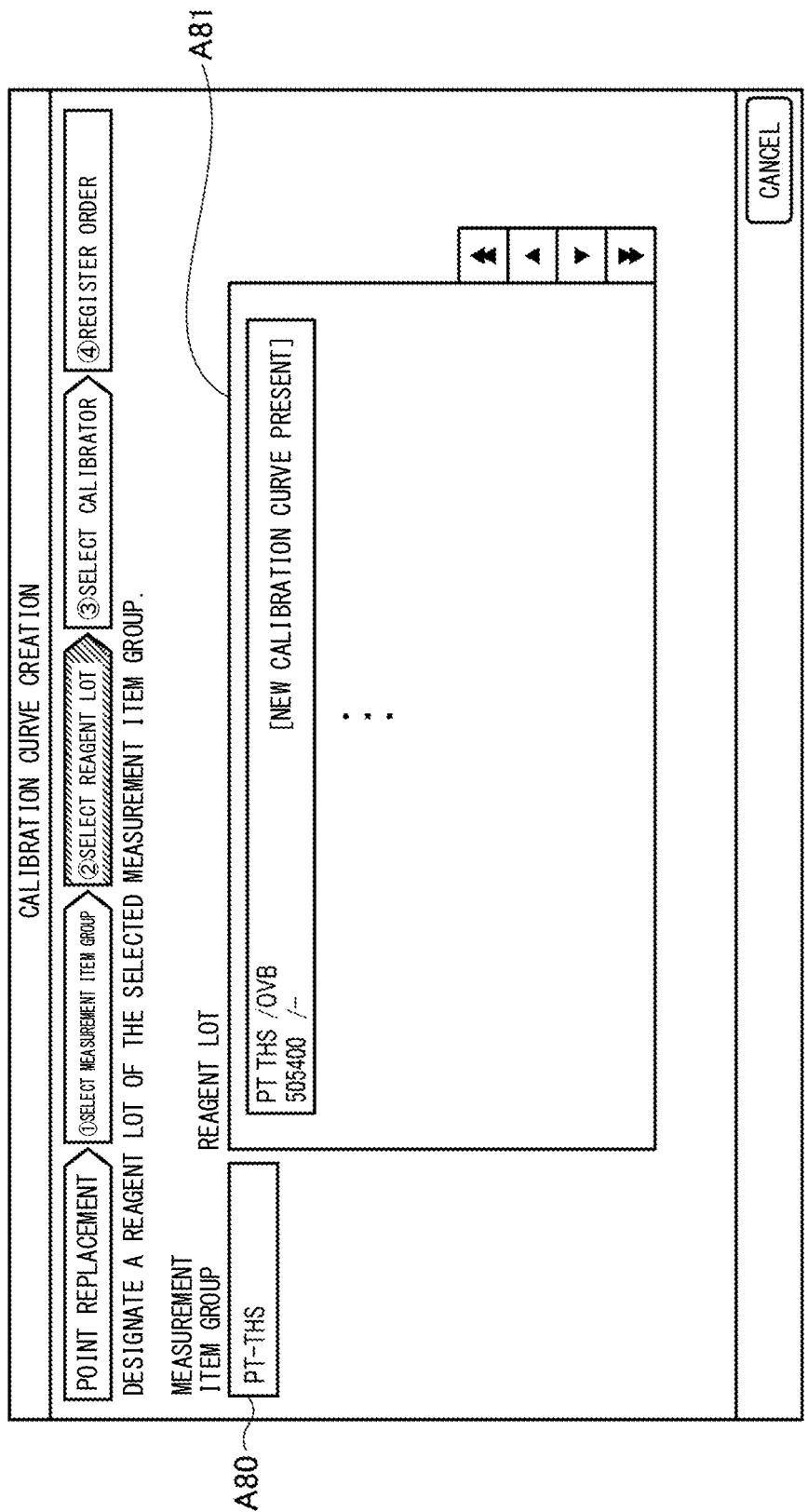
FIG. 15 shows one example of a screen for receiving selection of a reagent lot.

FIG. 15 shows one example of the screen for receiving selection of a reagent lot. The screen shown in FIG. 15 includes a display area A80 for displaying the measurement item group selected on the screen in FIG. 14, and a display area A81 for displaying a list of reagent lots having been used in creation of calibration curves of the measurement item group. The display controller 102 refers to the calibration curve DB 100a, extracts reagent lots recorded in "reagent lot" of the record including the measurement item group selected in FIG. 14, and displays a list of the extracted reagent lots in a display area A81. With reference back to FIG. 13, description is continued.

In step S22, the input reception unit 101 receives selection of a measurement item for which a measurement value is to be replaced, from among a plurality of measurement items displayed on the display unit 33. In step S23, the input reception unit 101 receives selection of a current measurement value that is to be replaced by a measurement value obtained through re-measurement, from among a plurality of measurement values displayed on the display unit 33.

Figure 16:
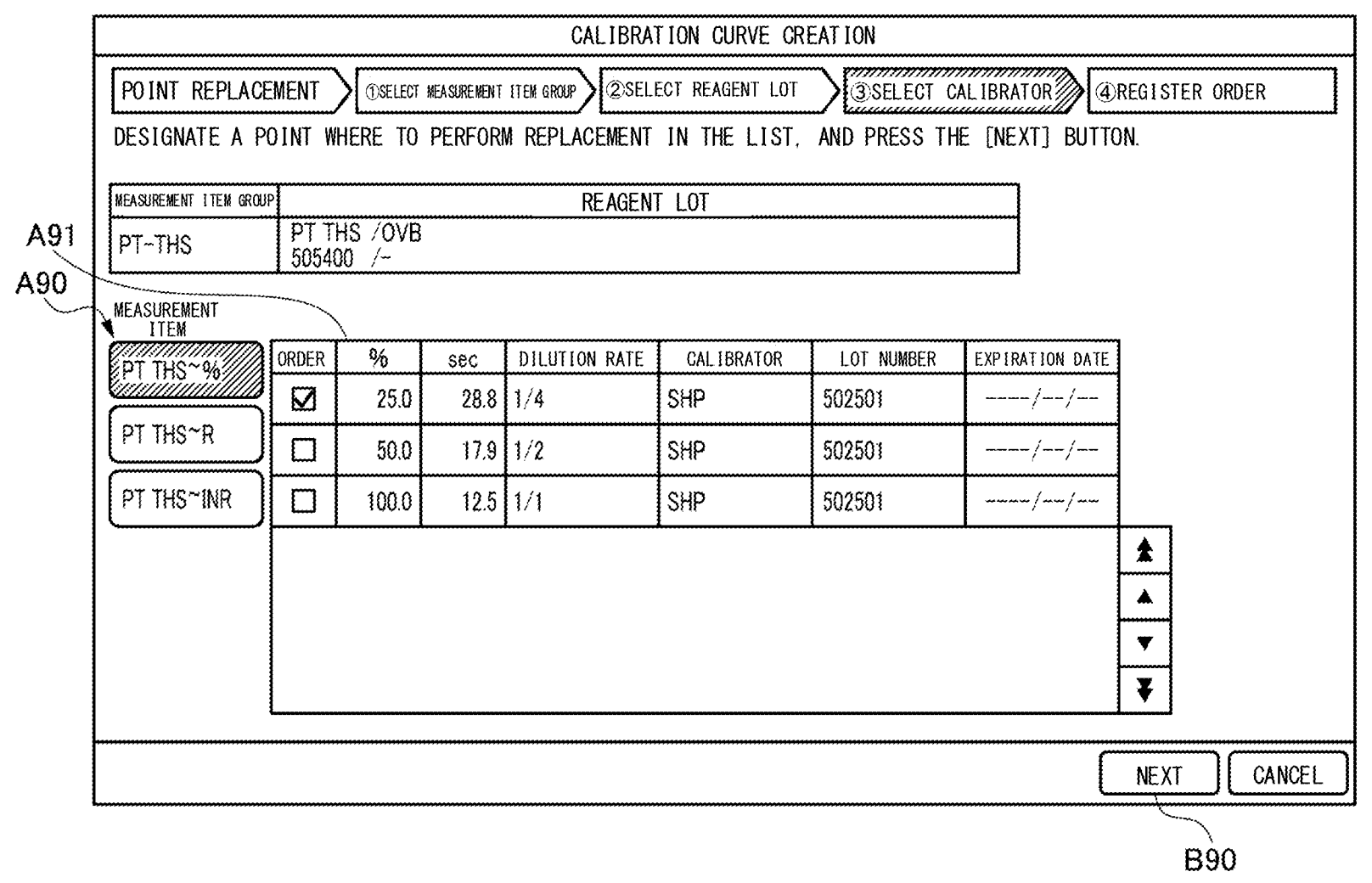

FIG. 16 shows one example of a screen for receiving selection of a measurement item for which a measurement value is to be replaced and the measurement value. The screen shown in FIG. 16 includes a display area A90 for displaying a button for receiving selection of a measurement item for which measurement is to be performed again with respect to the calibration curve for which a measurement value is to be replaced, and a display area A91 for displaying a current measurement value at each measurement point on the calibration curve with respect to the measurement item selected in the display area A90.

The display controller 102 refers to the calibration curve DB 100a, extracts measurement items recorded in "measurement item" of the record including the reagent lot selected in FIG. 15, and displays a list of the extracted measurement items in the display area A90. In addition, the display controller 102 extracts "calibrator", "calibrator lot number", "dilution rate", and "measurement value" from the record, and displays a list of the extracted data in the display area A91.

For example, on the screen in FIG. 16, "PT THS~%", "PT THS~R", and "PT THS~INR" are shown as the measurement items, and three measurement values (the coagulation rate at a concentration of 25% is 28.8 seconds, the coagulation rate at a concentration of 50% is 17.9 seconds, and the coagulation rate at a concentration of 100% (not diluted) is 12.5 seconds) corresponding to "PT THS~%" of the measurement item are displayed. The user selects a measurement item and a measurement value to be re-measured, on the screen shown in FIG. 16. In the example in FIG. 16, PT THS~%" is selected as the measurement item, and from the measurement value at the concentration of 25%, the measurement value at the concentration of 50%, and the measurement value at the concentration of 100%, the measurement value at the concentration of 25% is selected as the target for re-measurement.

Figure 17:
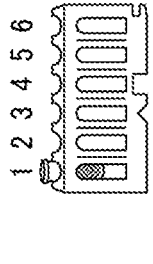
FIG. 17 shows one example of a screen for receiving designation of a specimen rack holding a specimen container.
Figure 18:
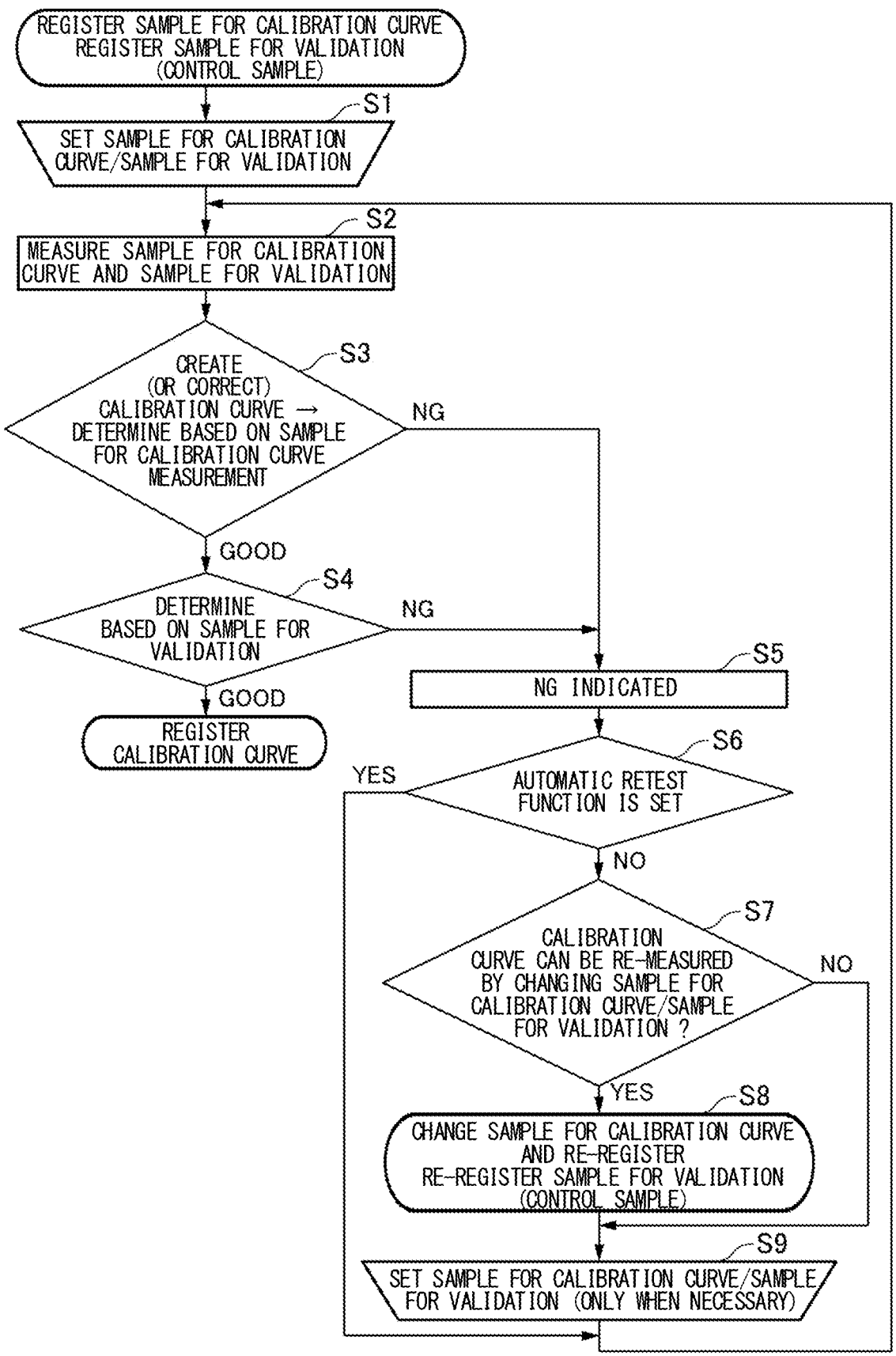
FIG. 18 is a diagram for describing a background technology.

In step S24, the input reception unit 101 receives, from the user, an input of a rack number of a specimen rack 42 in which a specimen container 41 holding a calibrator to be used in the re-measurement is inserted. FIG. 17 shows one example of a screen for receiving an input of a rack number. The screen shown in FIG. 17 includes an input area A100 for inputting a rack number, and a display area A101 for designating, to the user, the position to which the specimen container 41 should be inserted among a plurality of insertion positions (six in the example in FIG. 17) of the specimen rack 42 having the inputted rack number. The user inserts the specimen container 41 holding the calibrator to be used in the re-measurement, at the position designated on the screen shown in FIG. 17, and presses a button B100.

In step S25, the measurement unit 22 accesses the calibration curve DB 100a, to obtain a dilution rate corresponding to the measurement value to be re-measured. For example, in the case shown on the screen in FIG. 16, the measurement unit 22 obtains ¼ (concentration of 25%) as the dilution rate.

In step S26, the measurement unit 22 measures measurement values by use of the calibrator in the specimen container 41 held at the rack position designated in the process procedure of step S24. More specifically, the preparation unit 21 dispenses, into a reaction chamber 43, the calibrator in the specimen container 41 held at the position designated in the process procedure of step S24, and injects a diluent to the calibrator having been dispensed into the reaction chamber 43, thereby diluting the dispensed calibrator to the concentration obtained in the process procedure of step S25. Subsequently, the preparation unit 21 generates a reagent by adding the reagent having the reagent lot designated in the process procedure of step S21. Subsequently, the measurement unit 22 measures measurement values, using the generated reagent. The measurement processing unit 103 calculates a measurement value, using the time series data obtained through the measurement performed by the measurement unit 22.

In step S27, after the measurement of the measurement value has ended (after calculation of the measurement value by the measurement processing unit 103 has been completed), the creation unit 104 creates a new calibration curve by replacing the measurement value before the re-measurement by the measurement value after the re-measurement. The display controller 102 causes the display unit 33 to display a screen for displaying the new calibration curve. The displayed screen is the same as the screen shown in FIG. 11, and thus, description thereof is omitted. After the process procedure of step S27 is completed, the measurement processing unit 103 performs blood coagulation analysis by comparing a measurement value of a specimen collected from a subject, with the new calibration curve.

<Modification>

In the process procedure described above, when selecting a calibration curve of which a measurement value is to be replaced, the user selects "point replacement" from the menu screen shown in FIG. 6, and further, needs to designate a measurement item group and a reagent lot on the screens shown in FIG. 14 and FIG. 15. However, the present disclosure is not limited thereto. For example, a configuration may be employed in which the display controller 102 displays a button for receiving an instruction for re-measurement on the screen shown in FIG. 11, and when the button is pressed, the measurement unit 22 performs re-measurement without receiving selection of a measurement item group and a reagent lot again. Alternatively, the display controller 102 may display a button for receiving an instruction for re-measurement, for each calibration curve point shown in the display area A61 or A62 in FIG. 11.

Further, after the button for receiving an instruction for re-measurement has been pressed, the display controller 102 may shift the screen to a screen for receiving designation of a rack position shown in FIG. 17. In this case, the measurement unit 22 may perform re-measurement by use of a calibrator at the rack position designated on the screen.

SUMMARY

In the blood analyzer 10 according to the present embodiment, a calibration curve is displayed, and among a plurality of measurement values having been used for creation of the calibration curve, a measurement value designated by a user is replaced with a measurement value obtained through re-measurement, and then a calibration curve is re-created and displayed. Accordingly, a measurement value suspected to be an error in the created calibration curve can be replaced, and the calibration curve can be quickly corrected.

In addition, in the blood analyzer 10 according to the present embodiment, when a measurement value to be re-measured designated by a user is measured again, the dilution rate corresponding to the designated measurement value is obtained from the calibration curve DB 100a, and the measurement is performed after the calibrator is diluted at the obtained dilution rate. Accordingly, when re-measuring the measurement value, the user can perform re-measurement without diluting the calibrator by himself/herself.

As described above, the blood analyzer 10 repeats, a plurality of times, a series of operations of: dispensing a calibrator from the same specimen container 41 into a reaction chamber 43; adjusting the concentration of the calibrator by adding a diluent to the reaction chamber 43; heating the reaction chamber 43; injecting a reagent into the reaction chamber 43; and measuring the coagulation process. At this time, if the amount of the calibrator held in the specimen container 41 is insufficient, the dilution rate of the calibrator measured in a latter half or at the end will fail to be identical to the prescribed dilution rate, and thus, an accurate calibration curve cannot be created. In such a case, as in the case of the conventional technology, if a specimen container 41 holding a sufficient amount of a calibrator is prepared again and measurement is performed again for all the measurement points, it takes time and cost. Meanwhile, in the present embodiment, a dilution rate corresponding to a designated measurement value is obtained from the calibration curve DB 100a, and the calibrator is diluted at the obtained dilution rate, and then, measurement is automatically performed. Accordingly, a calibration curve that includes a measurement value suspected to be an error can be corrected more quickly and at low cost.

The embodiment described is for facilitating understanding of the present disclosure, and is not for limiting the present disclosure. The flow charts, sequences, and elements of the embodiment, and the arrangements, materials, conditions, shapes, sizes, etc., thereof described in the embodiment are not limited to those which are shown as examples, and can be changed as appropriate. Components shown in different embodiments can be partially replaced with each other, or can be combined with each other.

For example, the present disclosure may include a configuration such that when the blood analyzer automatically finds an abnormal point (a first measurement value) in the calibration curve (for example, when there is a point which is too far from the approximate expression of the calibration curve), it automatically selects the abnormal point (a first measurement value) in the calibration curve and dispenses the calibrator again, adjusts it to the same dilution rate as that of the abnormal point, re-measures and replaces the abnormal point (a first measurement value) with the newly obtained measurement value (a second measurement value).

What is claimed is:

1. A calibration curve creation method performed by an analyzer, the calibration curve creation method comprising:
preparing, by the analyzer, a plurality of specimens that include samples of calibrator, respectively, at different dilution rates;
repeating, by the analyzer, a measurement at a number of the different dilution rates to measure each of the plurality of specimens to derive sets of time series data corresponding, respectively, to the different dilution rates;
repeating, by the analyzer, an analysis at the number of the different dilution rates to analyze each set of time series data to derive, and store in a memory, a first set of calibration curve points corresponding, respectively, to the different dilution rates;
subsequent to storing the first set of calibration curve points in the memory, performing a point correction process by the analyzer for each initiation of the point correction process, wherein the point correction process is executed to correct a calibration curve point in the first set of calibration points and comprises following steps (a), (b), (c), (d), (e) and (f):
(a) displaying, by the analyzer, a point selection screen that shows the first set of calibration curve points retrieved from the memory for a selection of one calibration curve point to be corrected among the first set of calibration curve points;
(b) in response to a selection of one calibration curve point from the first set of calibration curve points, displaying, by the analyzer, an input screen that requests an input of a rack identifier of a specimen rack and a position identifier of an insertion position in the specimen rack;
(c) preparing, by the analyzer, a re-measurement specimen that includes a quantity of the calibrator at the dilution rate that corresponds to the selected one calibration curve point, wherein the re-measurement specimen is prepared from the calibrator in a container that has been inserted by a user in the identified insertion position of the identified specimen rack;
(d) measuring, by the analyzer, the quantity of the calibrator in the re-measurement specimen to derive a new set of time series data corresponding to the selected one calibration curve point;
(e) analyzing, by the analyzer, the new set of time series data to derive a new calibration curve point corresponding to the selected one calibration curve point; and
(f) replacing, by the analyzer, the selected one calibration curve point in the memory with the new calibration curve point to update the first set of calibration curve points to a second set of calibration curve points.

2. The calibration curve creation method of claim 1, wherein the point selection screen shows the first set of calibration curve points in association, respectively, with the different dilution rates.

3. The calibration curve creation method of claim 1, wherein each calibration curve point of the first set of calibration curve points shown on the point selection screen has a significant figure of not less than 1 digit and not greater than 4 digits.

4. The calibration curve creation method of claim 1, wherein the plurality of specimens are each prepared by diluting the calibrator at a different dilution rate of less than 100-fold.

5. The calibration curve creation method of claim 1, wherein each calibration curve point of the first set of calibration curve points is associated with a time duration measured during blood coagulation.

6. The calibration curve creation method of claim 1, wherein step (c) comprises mixing the quantity of the calibrator with a reagent for blood coagulation analysis at a dilution rate that corresponds to the selected one calibration curve point.

7. The calibration curve creation method of claim 1, further comprising analyzing, after step (f), a specimen collected from a subject by application of the second set of calibration curve points.

8. The calibration curve creation method of claim 7, wherein analyzing a specimen collected from a subject comprises performing blood coagulation analysis.

9. The calibration curve creation method of claim 1, wherein performing the point correction process comprises performing the point correction process in response to an instruction from the user.

10. An analyzer comprising:
a preparation unit configured to prepare a plurality of specimens that include samples of calibrator, respectively, at different dilution rates;
a measurement unit configured to repeat a measurement at a number of the different dilution rates to measure each of the plurality of specimens to obtain sets of time series data corresponding, respectively, to the different dilution rates;
a controller configured to repeat an analysis at the number of the different dilution rates to analyze each set of time series data to derive, and store in a memory, a first set of calibration curve points corresponding, respectively, to the different dilution rates; and
the controller further configured to, subsequent to storing the first set of calibration curve points in the memory, perform a point correction process for each initiation of the point correction process, wherein the point correction process is executed to correct a calibration point in the first set of the calibration curve points and comprises following steps (a), (b), (c), (d), (e) and (f):
(a) displaying a point selection screen that shows the first set of calibration curve points retrieved from the memory for a selection of one point from the first set of calibration curve points to be corrected;
(b) in response to a selection of one calibration curve point from the first set of calibration curve points, displaying an input screen that requests an input of a rack identifier of a specimen rack and a position identifier of an insertion position in the specimen rack;
(c) preparing a re-measurement specimen that includes a quantity of the calibrator at a dilution rate corresponding to the selected one calibration curve point, wherein the re-measurement specimen is prepared from the calibrator that has been inserted by a user in the identified insertion position of the identified specimen rack;
(d) measuring the quantity of the calibrator in the re-measurement specimen and obtaining a new set of time series data corresponding to the selected one calibration curve point;
(e) analyzing the new set of time series data to derive a new calibration curve point corresponding to the selected one calibration curve point; and
(f) replacing the selected one calibration curve point in the memory with the new calibration point to update the first set of calibration curve points to a second set of calibration curve points.

11. The analyzer of claim 10, wherein the point selection screen shows the first set of calibration curve points in association, respectively, with the different dilution rates.

12. The analyzer of claim 10, wherein each calibration curve point of the first set of calibration curve points has a significant figure of not less than 1 digit and not greater than 4 digits.

13. The analyzer of claim 10, wherein the plurality of specimens are each prepared by diluting the calibrator at a different dilution rate of less than 100-fold.

14. The analyzer of claim 10, wherein each calibration curve point of the first set of calibration curve points is associated with a time duration measured during blood coagulation.

15. The analyzer of claim 10, wherein step (c) comprises mixing the quantity of the calibrator with a reagent for blood coagulation analysis at the dilution rate that corresponds to the selected one calibration curve rate.

16. The analyzer of claim 10, wherein the controller is configured to analyze, after the controller performs step (f) a specimen collected from a subject by application of the second set of calibration curve points.

17. The analyzer of claim 16, wherein the controller is configured to analyze the specimen collected from the subject to perform blood coagulation analysis.

18. The analyzer of claim 10, wherein the controller is configured to perform the point correction process in response to an instruction from the user.

19. A non-transitory storage medium storing a computer program executable by an analyzer to implement:
preparing, by the analyzer, a plurality of specimens that include samples of calibrators, respectively, at different dilution rates;
repeating, by the analyzer, a measurement at a number of the different dilution rates to measure each of the plurality of specimens to obtain sets of time series data corresponding, respectively, to the different dilution rates;
repeating, by the analyzer, an analysis at the number of the different dilution rates to analyze each set of time series to derive, and store in a memory, a first set of calibration curve points corresponding, respectively, to the different dilution rates;
subsequent to storing the first set of calibration curve points in the memory, performing a point correction process by the analyzer for each initiation of the point correction process, wherein the point correction process is executed to correct a calibration curve point in the first set of calibration curve points and comprises following steps (a), (b), (c), (d), (e) and (f):
(a) displaying, by the analyzer, a point selection screen that shows the first set of calibration curve points retrieved from the memory for a selection of one calibration curve point to be corrected among the first set of calibration curve points;

(b) in response to a selection of one calibration curve point from the first set of calibration curve points, displaying, by the analyzer, an input screen that requires an input of a rack identifier of a specimen rack and a position identifier of an insertion position of the specimen rack;

(c) preparing, by the analyzer, a re-measurement specimen that includes a quantity of the calibrator at the dilution rate corresponding to the selected one calibrator curve point, wherein the re-measurement specimen is prepared from the calibrator in a container that has been inserted by a user in the identified insertion position of the identified specimen rack;

(d) measuring, by the analyzer, the quantity of the calibrator in the re-measurement specimen to derive a new set of time series data corresponding to the selected one calibration curve point;

(e) analyzing, by the analyzer, the new set of time series data to derive a new calibration point corresponding to the selected one calibration curve point; and (f) replacing, by the analyzer, the selected one calibration curve point in the memory with the new calibration curve point to update the first set of calibration curve points to a second set of calibration curve points.

20. The non-transitory storage medium of claim 19, wherein the point selection screen shows the first set of calibration curve points in association, respectively, with the different dilution rates.

* * * * *